(12) United States Patent
Nishioka

(10) Patent No.: US 12,091,308 B2
(45) Date of Patent: Sep. 17, 2024

(54) MICROCHANNEL CHIP AND METHOD FOR MANUFACTURING SAME

(71) Applicant: ZEON CORPORATION, Tokyo (JP)

(72) Inventor: Hiroya Nishioka, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 201 days.

(21) Appl. No.: 17/998,492

(22) PCT Filed: May 24, 2021

(86) PCT No.: PCT/JP2021/019664
§ 371 (c)(1),
(2) Date: Nov. 11, 2022

(87) PCT Pub. No.: WO2021/241516
PCT Pub. Date: Dec. 2, 2021

(65) Prior Publication Data
US 2023/0212000 A1 Jul. 6, 2023

(30) Foreign Application Priority Data
May 29, 2020 (JP) ................................. 2020-094889

(51) Int. Cl.
*B32B 27/02* (2006.01)
*B81B 1/00* (2006.01)
*B81C 3/00* (2006.01)

(52) U.S. Cl.
CPC ............... *B81B 1/00* (2013.01); *B81C 3/001* (2013.01); *B81C 2203/036* (2013.01)

(58) Field of Classification Search
CPC ..... C04B 41/009; C04B 41/478; C04B 33/00; C04B 35/00; C04B 41/4521;
(Continued)

(56) References Cited

U.S. PATENT DOCUMENTS

2016/0052238 A1  2/2016  Taniguchi

FOREIGN PATENT DOCUMENTS

| CA | 3153549 A1 | 4/2020 |
|---|---|---|
| JP | 2008304352 A | 12/2008 |
| JP | 5948248 B2 | 7/2016 |
| WO | 2014178439 A1 | 11/2014 |

OTHER PUBLICATIONS

Matsumoto, JP 2004074339 A (Year: 2004).*
(Continued)

*Primary Examiner* — Lawrence D Ferguson
(74) *Attorney, Agent, or Firm* — KENJA IP LAW PC (57) ABSTRACT

A microchannel chip with which channel deformation does not occur even when high-temperature and high-pressure sterilization treatment is performed and with which strong joining performance of substrates is maintained; and a method for manufacturing the same are provided. A microchannel chip comprising: a channel substrate having a microchannel formed on at least one surface thereof; a lid substrate; and a joining layer joining the channel substrate and the lid substrate, wherein the channel substrate, the lid substrate, and the joining layer are each formed of a cycloolefin polymer, a glass-transition temperature $Tg_{s1}$ of a cycloolefin polymer forming the channel substrate, a glass-transition temperature $Tg_{s2}$ of a cycloolefin polymer forming the lid substrate, and a glass-transition temperature $Tg_2$ of a cycloolefin polymer forming the joining layer have relationships: $Tg_{s1}>Tg_2$; and $Tg_{s2}>Tg_2$, and the joining layer has a thickness within a specific range.

5 Claims, 2 Drawing Sheets (58) Field of Classification Search
CPC ..... B01L 2200/0689; B01L 2300/0816; B01L 2300/0887; B01L 2300/12; B01L 3/502707; B29C 65/02; B29C 65/18; B29C 65/4815; B29C 66/02241; B29C 66/026; B29C 66/1122; B29C 66/53461; B29C 66/71; B29C 66/723; B29C 66/73117; B29C 66/73118; B29C 66/7392; B29C 66/73921; B29C 66/8322; B29C 66/836; B29C 66/91943; B29C 66/91945; B29K 2023/38; B29L 2031/753; B29L 2031/756; B81B 1/00; B81C 2203/036; B81C 3/001; G01N 33/48707
See application file for complete search history.

(56) References Cited

OTHER PUBLICATIONS

Dec. 20, 2023, the Extended European Search Report issued by the European Patent Office in the corresponding European Patent Application No. 21813580.4.

Nov. 17, 2022, International Preliminary Report on Patentability issued in the International Patent Application No. PCT/JP2021/019664.

* cited by examiner

[Units: mm]

FIG. 3B

MICROCHANNEL CHIP AND METHOD FOR MANUFACTURING SAME

TECHNICAL FIELD

The present disclosure relates to a microchannel chip and a method for manufacturing the same.

BACKGROUND

In recent years, chips (microchannel chips) having fine channels or reactors on the order of micrometers formed by microprocessing techniques have been used in various fields for analysis and testing of biological substances such as DNA, RNA, and proteins, drug discovery/pharmaceutical development, organic synthesis, water quality analysis, and so forth.

Moreover, resin microchannel chips, which can be produced at low cost, have attracted attention.

A resin microchannel chip may be produced by arranging a joining layer between a resin substrate having a microchannel formed on at least one surface thereof and a resin lid substrate serving as a lid material and performing heating thereof to cause joining (for example, refer to Patent Literature (PTL) 1 to 4).

CITATION LIST

Patent Literature

PTL 1: JP5948248B2
PTL 2: JP2008-304352A
PTL 3: JP5948248B2
PTL 4: WO2014/178439A1

SUMMARY

Technical Problem

In a situation in which a microchannel chip is subjected to high-temperature and high-pressure sterilization treatment such as steam sterilization treatment, for example, a problem of channel deformation may arise during sterilization treatment when a thick joining layer is adopted. Moreover, an adhesive material other than a cycloolefin polymer has conventionally been used in order to achieve strong joining performance of substrates in a microchannel chip produced using a cycloolefin polymer having transparency and low autofluorescence as a substrate material, and thus such microchannel chips have suffered from a problem of noise caused by autofluorescence of the adhesive material during optical signal detection. Up until the present, there has been no known microchannel chip in which every member has been formed from a cycloolefin polymer and in which strong joining performance of substrates has been maintained without using an adhesive material such as an autofluorescent material.

Accordingly, an object of the present disclosure is to provide a microchannel chip and method for manufacturing the same with which channel deformation does not occur even when high-temperature and high-pressure sterilization treatment is performed and with which strong joining performance of substrates is maintained even when using cycloolefin polymer as a material for the entire microchannel chip.

Solution to Problem

As a result of diligent research aimed at solving the problem set forth above, the inventor discovered that by adopting a thin film as a joining layer, it is possible to inhibit channel deformation caused by high-temperature and high-pressure sterilization treatment, and that by using cycloolefin polymers having specific glass-transition temperature relationships as materials of substrates and a joining layer, it is possible to maintain strong joining performance of the substrates. In this manner, the inventor completed the present disclosure.

Thus, the present disclosure provides the following microchannel chips and methods for manufacturing the same.

{1} A microchannel chip comprising: a channel substrate having a microchannel formed on at least one surface thereof; a lid substrate; and a joining layer joining the channel substrate and the lid substrate, wherein the channel substrate, the lid substrate, and the joining layer are each formed of a cycloolefin polymer, a glass-transition temperature $Tg_{s1}$ of a cycloolefin polymer forming the channel substrate, a glass-transition temperature $Tg_{s2}$ of a cycloolefin polymer forming the lid substrate, and a glass-transition temperature $Tg_2$ of a cycloolefin polymer forming the joining layer have relationships:

$Tg_{s1} > Tg_2$; and $Tg_{s2} > Tg_2$, and the joining layer has a thickness of less than 50 μm.

{2} The microchannel chip according to the foregoing {1}, wherein $Tg_{s1}$ and $Tg_{s2}$ are each 125° C. or higher, $Tg_{s1} \geq Tg_2 + 10°$ C., and $Tg_{s2} \geq Tg_2 + 10°$ C.

{3} A method for manufacturing the microchannel chip according to the foregoing {1} or {2}, comprising joining a channel substrate and a lid substrate via a joining layer by thermal fusion.

{4} The method according to the foregoing {3}, comprising:

a step of forming a joining layer on at least one of a substrate for channel formation and a lid substrate;

a step of forming a channel on a substrate for channel formation having a joining layer formed thereon or a substrate for channel formation not having a joining layer formed thereon so as to form a channel substrate having a joining layer formed thereon or a channel substrate not having a joining layer formed thereon; and a step of joining, via a joining layer by thermal fusion, at least one combination among: a combination of a channel substrate having a joining layer formed thereon and a lid substrate not having a joining layer formed thereon; a combination of a channel substrate not having a joining layer formed thereon and a lid substrate having a joining layer formed thereon; and a combination of a channel substrate having a joining layer formed thereon and a lid substrate having a joining layer formed thereon.

{5} The method according to the foregoing {3}, comprising:

a step of forming a channel substrate having a channel formed on at least one surface thereof;

a step of forming a joining layer on at least one surface of at least one of a channel substrate and a lid substrate at a section of the surface that is not a section corresponding to a channel; and a step of joining, via a joining layer by thermal fusion, at least one combination among: a combination of a channel substrate having a joining layer formed thereon and a lid substrate not having a joining layer formed thereon; a combination of a channel substrate not having a joining layer formed thereon and a lid substrate having a joining layer formed thereon; and a combination of a channel substrate having a joining layer formed thereon and a lid substrate having a joining layer formed thereon.

Advantageous Effect

According to the present disclosure, it is possible to provide a microchannel chip and method for manufacturing the same with which channel deformation does not occur even when high-temperature and high-pressure sterilization treatment is performed and with which strong joining performance of substrates is maintained.

DETAILED DESCRIPTION

The following provides a detailed description of embodiments of the present disclosure.

(Microchannel Chip)

A presently disclosed microchannel chip includes a channel substrate s1 having a microchannel formed on at least one surface thereof, a lid substrate s2, and a joining layer joining the channel substrate s1 and the lid substrate s2. Moreover, in the presently disclosed microchannel chip, the channel substrate s1, the lid substrate s2, and the joining layer are each formed of a cycloolefin polymer, a glass-transition temperature $Tg_{s1}$ of a cycloolefin polymer forming the channel substrate, a glass-transition temperature $Tg_{s2}$ of a cycloolefin polymer forming the lid substrate, and a glass-transition temperature $Tg_2$ of a cycloolefin polymer forming the joining layer have relationships:

$Tg_{s1} > Tg_2$; and $Tg_{s2} > Tg_2$, and the joining layer has a thickness of less than 50μ.

<Channel Substrate>

A substrate made of a cycloolefin polymer that has a microchannel formed on at least one surface thereof can be used as the channel substrate. The channel substrate is joined to the lid substrate with a surface at which the microchannel is formed as a joining surface.

The microchannel width, depth, and shape can be changed as appropriate depending on the application of the microchannel chip, but are normally on the order of millimeters or smaller, and are preferably on the order of micrometers, though they may even be on the order of nanometers. Specifically, the microchannel width can be set as not less than 10 μm and not more than 800 μm, for example, but is not specifically limited thereto.

The formation of a microchannel on a substrate made of a cycloolefin polymer can be achieved by a microprocessing technique such as photolithography or thermal imprinting, cutting, injection molding, or the like, for example. Moreover, channel formation may be performed with respect to a substrate for channel formation not having a joining layer formed thereon, or may be performed with respect to a substrate for channel formation after formation of a joining layer. The formation of a channel with respect to a substrate for channel formation not having a joining layer formed thereon can be achieved by a microprocessing technique such as photolithography or thermal imprinting, cutting, injection molding, or the like, for example. The formation of a channel with respect to a substrate for channel formation after formation of a joining layer can be achieved by adopting a microprocessing technique such as photolithography or thermal imprinting, cutting, or the like with respect to a surface of the substrate for channel formation at which the joining layer has been formed, for example.

<Lid Substrate>

Any substrate made of a cycloolefin polymer that can cover the microchannel formed on the channel substrate can be used as the lid substrate. Specifically, the lid substrate may be a substrate having a smooth surface that can cover the channel substrate and optionally having a through hole that serves as an injection port for a sample or the like into the microchannel of the channel substrate when the substrate is used with the channel substrate to form the microchannel chip. The lid substrate is joined to the channel substrate with the smooth surface side thereof as a joining surface. Note that the lid substrate may be a substrate having a microchannel formed on a surface at the opposite side thereof to a smooth surface side that is joined to the channel substrate.

The formation of a through hole in a substrate made of a cycloolefin polymer can be achieved by a microprocessing technique such as photolithography or thermal imprinting, cutting, injection molding, or the like, for example. Moreover, through hole formation may be performed with respect to a substrate for channel formation not having a joining layer formed thereon, or may be performed with respect to a substrate for channel formation after formation of a joining layer. The formation of a through hole with respect to a substrate for channel formation not having a joining layer formed thereon can be achieved by a microprocessing technique such as photolithography or thermal imprinting, cutting, injection molding, or the like, for example. The formation of a through hole with respect to a substrate for channel formation after formation of a joining layer can be achieved by adopting a microprocessing technique such as photolithography or thermal imprinting, cutting, or the like with respect to a surface of the substrate for channel formation at which the joining layer has been formed, for example.

<Joining Layer>

The joining layer is a member that is formed on the channel substrate or the lid substrate and that is for joining the channel substrate and the lid substrate.

The thickness of the joining layer is less than 50 μm, preferably 40 μm or less, more preferably 10 μm or less, and even more preferably 5 μm or less. When the joining layer has a thinner thickness, channel deformation is inhibited during steam sterilization treatment of the microchannel chip as a result of the joining layer being a thin film. The thickness of the joining layer should be of a minimum thickness that makes it possible to ensure adhesiveness of the channel substrate and the lid substrate and may, for example, be 0.1 μm or more, preferably 0.12 μm or more, more preferably 0.15 μm or more, and even more preferably 0.2 μm or more.

A ratio of the thickness of the joining layer relative to the channel depth may, for example, be 0.1/100 or more, preferably 0.12/100 or more, more preferably 0.15/100 or more, and even more preferably 0.2/100 or more. Moreover, the ratio of the thickness of the joining layer relative to the channel depth may, for example, be 50/100 or less, preferably 30/100 or less, more preferably 20/100 or less, and even more preferably 10/100 or less.

<Materials of Channel Substrate, Lid Substrate, and Joining Layer>

Cycloolefin polymers are used as materials of the channel substrate, the lid substrate, and the joining layer. A cycloolefin polymer has little reduction of joint strength over time and reduction of optical stability due to water absorption, and thus is suitable for a microchannel chip having excellent durability. Moreover, a cycloolefin polymer is a material having transparency and low autofluorescence, and thus is suitable for detection of an optical signal from a microchannel of a microchannel chip. By using cycloolefin polymers as all materials of the microchannel chip and by not using an adhesive material such as an autofluorescent material, it is possible to suppress noise due to autofluorescence of an adhesive material during optical signal detection. The cycloolefin polymers used as materials of the channel substrate, the lid substrate, and the joining layer satisfy glass-transition temperature relationships described below. As a result of such glass-transition temperature relationships being satisfied, it is possible to maintain strong joining performance of substrates even when cycloolefin polymers are used as all materials of the microchannel chip. The types of cycloolefin polymers used as materials of the channel substrate, the lid substrate, and the joining layer may be selected as appropriate from specific examples described further below, for example, such that the aforementioned glass-transition temperature relationships are satisfied. The cycloolefin polymers used as materials of the channel substrate, the lid substrate, and the joining layer are preferably cycloolefin polymers having a water absorption of 0.01 mass % or less. The cycloolefin polymers used as materials of the channel substrate and the lid substrate may be of the same type or may be of different types.

<<Glass-Transition Temperatures of Cycloolefin Polymers>>

Relationships of the glass-transition temperature $Tg_{s1}$ of a cycloolefin polymer that is a material of the channel substrate s1, the glass-transition temperature $Tg_{s2}$ of a cycloolefin polymer that is a material of the lid substrate s2, and the glass-transition temperature $Tg_2$ of a cycloolefin polymer that is a material of the joining layer satisfy the following:

$Tg_{s1} > Tg_2$; and $Tg_{s2} > Tg_2$.

As a result of the above relationships being satisfied, it is possible to cause softening of only the joining layer without softening, deformation, or deterioration of the channel substrate and the lid substrate and to cause joining by thermal fusion in production of the microchannel chip by performing joining of the channel substrate and the lid substrate at a temperature that is higher than $Tg_2$ and lower than $Tg_{s1}$ and $Tg_{s2}$.

$Tg_{s1}$ is preferably 125° C. or higher, and more preferably 130° C. or higher. Through $Tg_{s1}$ being within a range such as set forth above, it is possible to inhibit softening, deformation, or deterioration of the channel substrate caused by heating (for example, autoclaving) during production and sterilization of the microchannel chip. Moreover, $Tg_{s1}$ is preferably 180° C. or lower, and more preferably 160° C. or lower. In this case, the difference between $Tg_{s1}$ and $Tg_2$ is preferably 10° C. or more (i.e., $Tg_{s1} \geq Tg_2 + 10°$ C.), more preferably 15° C. or more (i.e., $Tg_{s1} \geq Tg_{2+15}°$ C.), and even more preferably 20° C. or more (i.e., $Tg_{s1} \geq Tg_2 + 20°$ C.). As the difference between $Tg_{s1}$ and $Tg_2$ increases, it becomes easier to set a heating temperature in order that only the joining layer softens without softening, deformation, or deterioration of the channel substrate in production of the microchannel chip. Moreover, the difference between $Tg_{s1}$ and $Tg_2$ is preferably 100° C. or less, more preferably 90° C. or less, and even more preferably 80° C. or less. As the difference between $Tg_{s1}$ and $Tg_2$ decreases, temperature stability of the joining layer improves.

$Tg_{s2}$ is preferably 125° C. or higher, and more preferably 130° C. or higher. Through $Tg_{s2}$ being within a range such as set forth above, it is possible to inhibit softening, deformation, or deterioration of the lid substrate caused by heating (for example, autoclaving) during production and sterilization of the microchannel chip. Moreover, $Tg_{s2}$ is preferably 180° C. or lower, and more preferably 160° C. or lower. In this case, the difference between $Tg_{s2}$ and $Tg_2$ is preferably 10° C. or more (i.e., $Tg_{s2} \geq Tg_2 + 10°$ C.), more preferably 15° C. or more (i.e., $Tg_{s2} \geq Tg_2 + 15°$ C.), and even more preferably 20° C. or more (i.e., $Tg_{s2} \geq Tg_2 + 20°$ C.). As the difference between $Tg_{s2}$ and $Tg_2$ increases, it becomes easier to set a heating temperature in order that only the joining layer softens without softening, deformation, or deterioration of the lid substrate in production of the microchannel chip. Moreover, the difference between $Tg_{s2}$ and $Tg_2$ is preferably 100° C. or less, more preferably 90° C. or less, and even more preferably 80° C. or less. As the difference between $Tg_{s2}$ and $Tg_2$ decreases, temperature stability of the joining layer improves.

$Tg_2$ is preferably 50° C. or higher, and more preferably 65° C. or higher. Through $Tg_2$ being within a range such as set forth above, temperature stability of the joining layer improves. Moreover, $Tg_2$ is preferably 130° C. or lower, more preferably 110° C. or lower, and even more preferably 100° C. or lower. Through $Tg_2$ being within a range such as set forth above, it is easier to set a heating temperature in order that only the joining layer softens in production of the microchannel chip.

The glass-transition temperature referred to in the present disclosure can be measured by differential scanning calorimetry (DSC) based on JIS-K7121.

<<Types of Cycloolefin Polymers>>

Each of the cycloolefin polymers may be a polymer or copolymer (hereafter, also referred to collectively using the term "polymer") that is obtained by polymerization of a monomer such as described below, or may be a hydrogenated product thereof, for example. The cycloolefin polymer may be crystalline or amorphous, but is preferably amorphous. It is preferable that a norbornene-based monomer is used as a monomer of the cycloolefin polymer. The norbornene-based monomer is a monomer having a norbornene ring. The norbornene-based monomer may be a bicyclic monomer such as bicyclo[2.2.1]hept-2-ene (commonly referred to as norbornene), 5-ethylidene-bicyclo[2.2.1]hept-2-ene (commonly referred to as ethylidene norbornene), or a derivative of either thereof (derivative having a substituent on a ring); a tricyclic monomer such as tricyclo[5.2.1.0$^{2,6}$] deca-3,8-diene (commonly referred to as dicyclopentadiene) or a derivative thereof; a tetracyclic monomer such as tetracyclo[7.4.0.0$^{2,7}$.1$^{10,13}$]tetradeca-2,4,6,11-tetraene (commonly referred to as methanotetrahydrofluorene), tetracyclo[6.2.1.1$^{3,6}$.0$^{2,7}$]dodec-4-ene (commonly referred to as tetracyclododecene), 9-ethylidenetetracyclo[6.2.1.1$^{3,6}$.0$^{2,7}$]dodec-4-ene, or a derivative of any thereof; or the like, for example. These monomers may have a substituent at any position. Examples of possible substituents include an alkyl group, an alkylene group, a vinyl group, an alkoxycarbonyl group, and an alkylidene group. The norbornene-based monomer may include two or more types of such substituents. Specific examples of derivatives include 8-methoxycarbonyl-tetracyclo[4.4.0.1$^{2,5}$.1$^{7,10}$]dodec-3-ene, 8-methyl-8-methoxycarbonyl-tetracyclo[4.4.0.1$^{2,5}$.1$^{7,10}$]dodec-3-ene, and 8-ethylidene-tetracyclo[4.4.0.1$^{2,5}$.1$^{7,10}$]dodec-3-ene. One of these norbornene-based monomers may be used individually, or two or more of these norbornene-based monomers may be used in combination. The cycloolefin polymer may be an addition polymer, a ring-opened polymer, or a hydrogenated product of either thereof, and is preferably a ring-opened polymer or a hydrogenated ring-opened polymer. In the case of a cycloolefin polymer that is used as a material of a substrate (channel substrate, lid substrate), it is preferable to use a polymer obtained by polymerization of monomer(s) among which the content of methanotetrahydrofluorene (MTF) is 25 parts by weight or more relative to 100 parts by weight, in total, of the monomer(s). In the case of a cycloolefin polymer used as a material of the joining layer, it is preferable to use a polymer obtained by polymerization of monomer(s) among which the content of dicyclopentadiene (DCPD) is 30 parts by weight or more relative to 100 parts by weight, in total, of the monomer(s).

The aforementioned ring-opened polymer can be produced by a method using a ring-opening polymerization catalyst. As the ring-opening polymerization catalyst, for example, a catalyst comprising a halide of a metal such as ruthenium or osmium, a nitrate or acetylacetone compound, and a reductant; or a catalyst comprising a halide of a metal such as titanium, zirconium, tungsten, or molybdenum or acetylacetone compound, and an organoaluminum compound. The ring-opened polymer can be produced by a method using a metathesis reaction catalyst (ring-opening polymerization catalyst) such as a ruthenium carbene complex catalyst described in WO2010/110323A1, a method using a ring-opening polymerization catalyst such as a tungsten(phenylimide)tetrachloride tetrahydrofuran complex or tungsten hexachloride described in JP2015-54885A, or the like, for example.

The aforementioned addition polymer can be obtained by polymerizing monomer(s) using a commonly known addition polymerization catalyst such as a catalyst comprising a titanium, zirconium, or vanadium compound and an organoaluminum compound. The addition polymer can be produced by, for example, performing addition copolymerization of a monomer of a cycloolefin polymer and, as necessary, a monomer (other monomer) that can be addition copolymerized, in the presence of a metallocene catalyst described in WO2017/199980A1.

Examples of other monomers that can be ring-opening copolymerized with a norbornene-based monomer include cycloolefin-based monomers that are monocyclic such as cyclohexene, cycloheptene, and cyclooctene.

One of these other monomers that can be ring-opening copolymerized with a norbornene-based monomer may be used individually, or two or more of these other monomers that can be ring-opening copolymerized with a norbornene-based monomer may be used in combination. In a case in which a norbornene-based monomer is ring-opening copolymerized with another monomer that can be ring-opening copolymerized therewith, appropriate selection is made such that, in the ring-opened polymer, the proportions of structural units derived from the norbornene-based monomer and structural units derived from the other monomer that can be ring-opening copolymerized are, as a weight ratio, normally within a range of 70:30 to 99:1, preferably within a range of 80:20 to 99:1, and more preferably within a range of 90:10 to 99:1.

Examples of other monomers that can be addition copolymerized with a norbornene-based monomer include α-olefins having a carbon number of 2 to 20 such as ethylene, propylene, 1-butene, 1-pentene, and 1-hexene, and derivatives thereof; cycloolefins such as cyclobutene, cyclopentene, cyclohexene, cyclooctene, and 3a,5,6,7a-tetrahydro-4,7-methano-1H-indene, and derivatives thereof; and non-conjugated dienes such as 1,4-hexadiene, 4-methyl-1,4-hexadiene, 5-methyl-1,4-hexadiene, and 1,7-octadiene. Of these other monomers, α-olefins are preferable, and ethylene is particularly preferable.

One of these other monomers that can be addition copolymerized with a norbornene-based monomer may be used individually, or two or more of these other monomers that can be addition copolymerized with a norbornene-based monomer may be used in combination. In a case in which a norbornene-based monomer is addition copolymerized with another monomer that can be addition copolymerized therewith, appropriate selection is made such that, in the addition polymer, the proportions of structural units derived from the norbornene-based monomer and structural units derived from the other monomer that can be addition copolymerized are, as a weight ratio, normally within a range of 30:70 to 99:1, preferably within a range of 50:50 to 97:3, and more preferably within a range of 70:30 to 95:5.

Moreover, the method by which a hydrogenated alicyclic structure-containing ring-opened polymer is produced by hydrogenation of a ring-opened polymer may be a method using a hydrogenation catalyst described in WO2010/110323A1, or the like, for example. For example, a hydrogenated alicyclic structure-containing ring-opened polymer can be produced by using a ruthenium carbene complex catalyst such as described above as a ring-opening polymerization catalyst in order to produce an alicyclic structure-containing polymer and then also using the ruthenium carbene catalyst in that form as a hydrogenation catalyst in order to hydrogenate the alicyclic structure-containing ring-opened polymer.

The glass-transition temperature (Tg) of a cycloolefin polymer can be adjusted as appropriate in accordance with the type(s) and mixing ratio of monomer(s) used in polymerization, the average molecular weight and molecular weight distribution of the polymer, and so forth.

In the presently disclosed microchannel chip, one or more of the channel substrate, the lid substrate, and the joining layer may include two or more layers of differing Tg.

(Method for Manufacturing Microchannel Chip)

The presently disclosed microchannel chip can be produced by a method described below (hereinafter, referred to as the "presently disclosed method"), for example.

The presently disclosed method includes joining a channel substrate and a lid substrate via a joining layer by thermal fusion.

In one embodiment, the presently disclosed method may be implemented by an order in which a joining layer is formed over the entire surface of a substrate and then a channel is subsequently formed on a substrate. In other words, the presently disclosed method may be implemented by the following steps.

Figure 1:
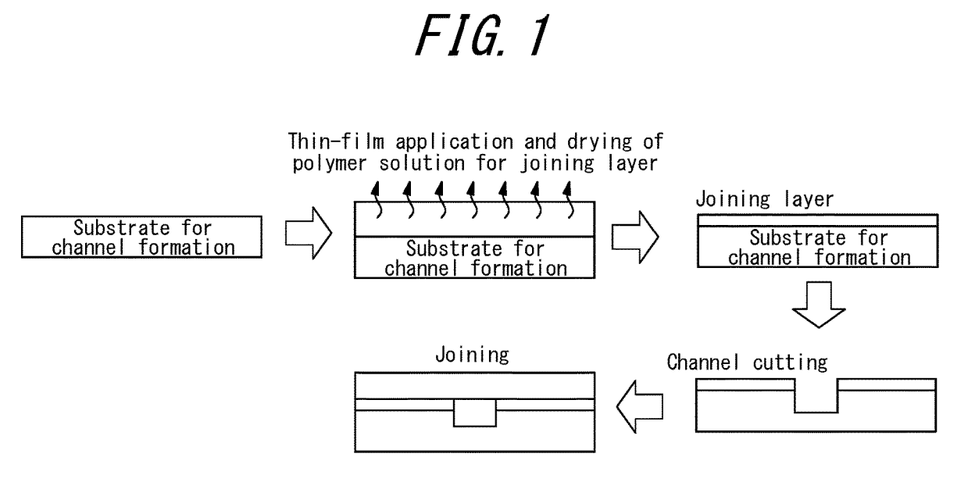
FIG. 1 is a conceptual diagram of a presently disclosed method for manufacturing a microchannel chip in which channel formation is performed after joining layer formation.

(1) A step of forming a joining layer on at least one of a substrate for channel formation and a lid substrate (2) A step of forming a channel by cutting, photolithography, or thermal imprinting, for example, on a substrate for channel formation having a joining layer formed thereon or a substrate for channel formation not having a joining layer formed thereon so as to form a channel substrate having a joining layer formed thereon or a channel substrate not having a joining layer formed thereon (3) A step of joining, via a joining layer by thermal fusion, at least one combination among: a combination of a channel substrate having a joining layer formed thereon and a lid substrate not having a joining layer formed thereon; a combination of a channel substrate not having a joining layer formed thereon and a lid substrate having a joining layer formed thereon; and a combination of a channel substrate having a joining layer formed thereon and a lid substrate having a joining layer formed thereon An example of a conceptual diagram of the method according to this embodiment is illustrated in FIG. 1.

In this embodiment, formation of a joining layer may be performed by applying a thin film of a solution of a cycloolefin polymer that serves as a material of the joining layer onto the entire surface of a substrate and then evaporating solvent. The solvent may be an organic solvent such as cyclohexane, tetrahydrofuran, toluene, xylene, decalin, methylcyclohexane, or ethylcyclohexane, for example, and any thereof may be used as a mixed solvent. Solvent evaporation may be performed by drying (for example, thermal drying or room temperature drying), thermal vacuum (reduced pressure) drying, or a combination thereof at a temperature that is lower than the glass-transition temperature of the cycloolefin polymer serving as a material of the joining layer, for example.

In a case in which a channel is to be formed on a substrate for channel formation having a joining layer formed thereon in this embodiment, channel formation is performed by processing the surface of the substrate for channel formation on which the joining layer has been formed by cutting, photolithography, thermal imprinting, or the like, for example, so as to remove a channel formation section of the substrate for channel formation, together with the joining layer.

In another embodiment, the presently disclosed method may be implemented by an order in which a substrate having a channel formed thereon (channel substrate) is produced and then a joining layer is formed on a surface of a substrate (channel substrate, lid substrate) at a section of the surface that is not a section corresponding to a channel. In other words, the presently disclosed method may be implemented by the following steps.

Figure 2:
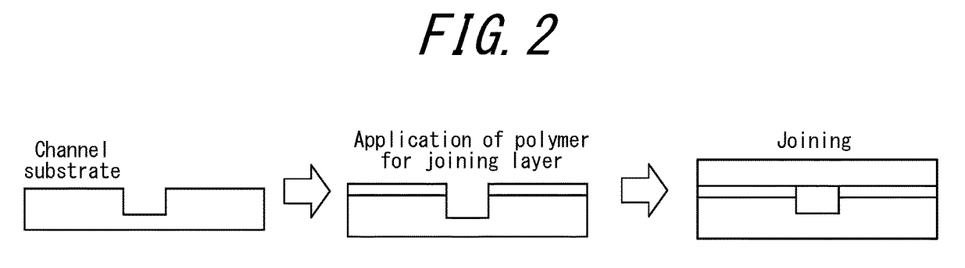
FIG. 2 is a conceptual diagram of a presently disclosed method for manufacturing a microchannel chip in which joining layer formation is performed after formation of a channel substrate having a channel formed thereon.

(1) A step of forming a channel substrate having a channel formed on at least one surface thereof (2) A step of forming a joining layer on at least one surface of at least one of a channel substrate and a lid substrate at a section of the surface that is not a section corresponding to a channel (3) A step of joining, via a joining layer by thermal fusion, at least one combination among: a combination of a channel substrate having a joining layer formed thereon and a lid substrate not having a joining layer formed thereon; a combination of a channel substrate not having a joining layer formed thereon and a lid substrate having a joining layer formed thereon; and a combination of a channel substrate having a joining layer formed thereon and a lid substrate having a joining layer formed thereon An example of a conceptual diagram of the method according to this embodiment is illustrated in FIG. 2.

In this embodiment, the channel substrate having a channel formed on at least one surface thereof may be formed by, for example, performing injection molding of a cycloolefin polymer serving as a material of the substrate, or may be formed by performing a microprocessing technique such as photolithography or thermal imprinting, or cutting, for example, with respect to a substrate for channel formation.

Moreover, formation of a joining layer in this embodiment may be performed by screen printing a solution of a cycloolefin polymer serving as a material of the joining layer at a section other than a section corresponding to a channel on a substrate or by masking a section corresponding to a channel on a substrate and performing spray coating of the solution so as to perform patterned coating, and then evaporating solvent.

From a viewpoint of ease of production, it is preferable that the presently disclosed method is implemented by an embodiment in which a joining layer is formed over the entire surface of a substrate.

Thermal fusion is performed by stacking a channel substrate and a lid substrate via a joining layer to form a temporarily fixed assembly, and then heating the temporarily fixed assembly to a temperature that is higher than $Tg_2$ and lower than $Tg_{s1}$ and $Tg_{s2}$. The means of thermal fusion may be autoclaving, hot pressing, roll pressing, or the like, for example. The temperature at which thermal fusion is performed is preferably $Tg_2+5°$ C. or higher, and more preferably $Tg_2+10°$ C. or higher. Moreover, the temperature at which thermal fusion is performed is preferably $Tg_2+50°$ C. or lower, and more preferably $Tg_2+40°$ C. or lower. Although it is preferable that before performing thermal fusion, trapped air is released from the temporarily fixed assembly and pressure bonding is performed, a small amount of air bubbles diffuse during autoclave processing, and thus a problem does not arise so long as a large amount of air is not trapped.

In the presently disclosed method, one or more of the channel substrate, the lid substrate, and the joining layer may include two or more layers of differing Tg.

EXAMPLES

The following provides a more specific description of the present disclosure based on examples. However, the present disclosure is not limited to the following examples.

<Methods for Measuring and Evaluating Physical Properties>

Measurements and evaluations of various physical properties were performed according to the following methods.

(Method for Measuring Weight-Average Molecular Weight Mw)

Weight-average molecular weight Mw was determined as a standard polyisoprene-equivalent value through measurement by gel permeation chromatography (GPC) with cyclohexane as an eluent. Standard polyisoprene produced by Tosoh Corporation was used as the standard polyisoprene. In a case in which the sample did not dissolve in cyclohexane, weight-average molecular weight Mw was determined as a standard polystyrene-equivalent value through measurement by GPC with tetrahydrofuran (THF) as an eluent. Standard polystyrene produced by Tosoh Corporation was used as the standard polystyrene.

(Method for Measuring Glass-Transition Temperature)

Glass-transition temperature (Tg) was measured using a differential scanning calorimeter (produced by SII Nano-Technology Inc.; product name: DSC6220SII) based on JIS-K7121 under conditions of a heating rate of 10° C./min.

[1-1. Production of Cycloolefin Polymers (COPs)]

<Production of COP-1>

(1-1-1) Production of Ring-Opened Polymer

At room temperature, 200 parts by weight of dehydrated cyclohexane, 0.75 mol % of 1-hexene, 0.15 mol % of diisopropyl ether, and 0.44 mol % of triisobutylaluminum relative to 100 parts by weight, in total, of subsequently described monomers were loaded into a glass reactor that had been internally purged with nitrogen and were mixed. Thereafter, 28 parts by weight of methanotetrahydrofluorene (MTF), 35 parts by weight of tetracyclododecene (TCD), and 37 parts by weight of dicyclopentadiene (DCPD) as monomers and 0.02 mol % of tungsten hexachloride (0.65 weight % toluene solution) were continuously added into the reactor over 2 hours, concurrently to one another, and polymerization was performed while maintaining a temperature of 45° C. Next, 0.2 mol % of isopropyl alcohol was added to the polymerization solution so as to deactivate the polymerization catalyst and stop the polymerization reaction. Note that amounts given in units of "mol %" in the preceding description are each a value for when the total amount of monomers is taken to be 100 mol %. The resultant norbornene-based ring-opened polymer had a weight-average molecular weight Mw of $2.8 \times 10^4$ and a molecular weight distribution (Mw/Mn) of 2.1. The conversion rate of monomers to polymer was 100%.

(1-1-2) Production of Norbornene-Based Cycloolefin Polymer (COP-1) by Hydrogenation Next, 300 parts by weight of a reaction solution containing the ring-opened polymer obtained by step (1-1-1) was transferred to a stirrer-equipped autoclave, 3 parts by weight of nickel catalyst loaded on diatomaceous earth (T8400RL produced by JGC C&C; nickel loading rate: 57%) was added, and a hydrogenation reaction was performed through 4 hours of autoclaving at a hydrogen pressure of 4.5 MPa and a temperature of 160° C.

Once the hydrogenation reaction had ended, the resultant solution was subjected to pressurized filtering (FUNDA-BAC Filter produced by Ishikawajima-Harima Heavy Industries Co., Ltd.) at a pressure of 0.25 MPa using Radiolite #500 as a filter bed so as to remove the hydrogenation catalyst and thereby obtain a colorless and transparent solution. The obtained solution was poured into a large amount of isopropanol to cause precipitation of a norbornene-based cycloolefin polymer (COP-1) as a hydrogenated ring-opened polymer. The norbornene-based cycloolefin polymer (COP-1) that precipitated was collected by filtration and was subsequently dried by a vacuum dryer (220° C., 1 Torr) for 6 hours to yield the norbornene-based cycloolefin polymer (COP-1). The norbornene-based cycloolefin polymer (COP-1) had a weight-average molecular weight of $3.5 \times 10^4$ and a molecular weight distribution Mw/Mn of 2.3.

The glass-transition temperature Tg of the obtained norbornene-based cycloolefin polymer (COP-1) was 134° C.

(1-1-3) Production of Thermoplastic Norbornene-Based Resin

The norbornene-based cycloolefin polymer (COP-1) obtained in step (1-1-2) was loaded into a twin-screw extruder and was molded into the form of a strand-like molded product by hot-melt extrusion molding. This molded product was finely cut using a strand cutter to obtain pellets of a thermoplastic norbornene-based resin that contained the norbornene-based cycloolefin polymer (COP-1).

<Production of COP-2>

A norbornene-based cycloolefin polymer (COP-2) and pellets of a thermoplastic norbornene-based resin containing the COP-2 were obtained in the same way as in production of COP-1 with the exception that 33 parts by weight of tetracyclododecene (TCD), 33 parts by weight of dicyclopentadiene (DCPD), and 34 parts by weight of norbornene (NB) were used as monomers. The COP-2 had a glass-transition temperature Tg of 70° C.

<Production of COP-3>

A norbornene-based cycloolefin polymer (COP-3) and pellets of a thermoplastic norbornene-based resin containing the COP-3 were obtained in the same way as in production of COP-1 with the exception that 22 parts by weight of tetracyclododecene (TCD), 73 parts by weight of dicyclopentadiene (DCPD), and 5 parts by weight of norbornene (NB) were used as monomers. The COP-3 had a glass-transition temperature Tg of 104° C.

<Production of COP-4>

A norbornene-based cycloolefin polymer (COP-4) and pellets of a thermoplastic norbornene-based resin containing the COP-4 were obtained in the same way as in production of COP-1 with the exception that 8 parts by weight of methanotetrahydrofluorene (MTF), 36 parts by weight of tetracyclododecene (TCD), and 56 parts by weight of dicyclopentadiene (DCPD) were used as monomers. The COP-4 had a glass-transition temperature Tg of 124° C.

<Production of COP-5>

A norbornene-based cycloolefin polymer (COP-5) and pellets of a thermoplastic norbornene-based resin containing the COP-5 were obtained in the same way as in production of COP-1 with the exception that 40 parts by weight of methanotetrahydrofluorene (MTF), 56 parts by weight of tetracyclododecene (TCD), and 4 parts by weight of dicyclopentadiene (DCPD) were used as monomers. The COP-5 had a glass-transition temperature Tg of 156° C.

[1-2. Production of Cycloolefin Copolymer (COC)]

Bicyclo[2.2.1]hept-2-ene (hereinafter, referred to as "NB") (120 kg) was added under a stream of nitrogen at normal temperature to a reactor that had been charged with 258 L of cyclohexane and was stirred for 5 minutes. In addition, triisobutylaluminum was added such that the concentration thereof in the system was 1.0 mL/L. Next, ethylene was passed at normal pressure under stirring so as to convert the system to an ethylene atmosphere. An autoclave internal temperature of 70° C. was maintained while raising the pressure with ethylene until the internal pressure reached a gauge pressure of 6 kg/cm$^2$. After 10 minutes of stirring, 0.4 L of a pre-prepared toluene solution containing isopropylidene(cyclopentadienyl)(indenyl)zirconium dichloride and methylalumoxane was added to the system to thereby initiate a copolymerization reaction of ethylene and NB. The catalyst concentration at this time was 0.018 mmol/L of isopropylidene(cyclopentadienyl)(indenyl)zirconium dichloride and 8.0 mmol/L of methylalumoxane relative to the overall system.

Ethylene was continuously supplied into the system during polymerization so as to maintain the temperature at 70°

C. and the internal pressure at a gauge pressure of 6 kg/cm'. Once 60 minutes had passed, isopropyl alcohol was added to stop the polymerization reaction. After depressurization, the polymer solution was removed, and then the polymer solution and an aqueous solution of 5 L of concentrated hydrochloric acid added to 1 m$^3$ of water were brought into contact under vigorous stirring in a ratio of 1:1 so as to cause catalyst residue to move into the aqueous phase. This contacted mixture was left to settle, the aqueous phase was then separated and removed, and water washing was performed twice to purify and separate the polymerization liquid phase.

Next, the polymerization liquid that had been purified and separated was brought into contact with 3 equivalents of acetone under vigorous stirring, copolymer was caused to precipitate, and then solid (copolymer) was collected by filtration and was thoroughly washed with acetone. This solid was added into acetone such as to be 40 kg/m$^3$ and was subsequently subjected to an extraction operation under conditions of 2 hours at 60° C. in order to extract unreacted monomer present in the polymer. After extraction treatment, solid was collected by filtration and was dried under nitrogen flow at 130° C. and 350 mmHg for 12 hours to yield an ethylene-NB copolymer (cycloolefin copolymer: COC). A twin-screw kneader was used to knead 100 parts by weight of the obtained ethylene-NB copolymer (COC) and 0.1 parts by weight of an antioxidant (Irganox® 1010 (Irganox is a registered trademark in Japan, other countries, or both)) and obtain pellets of a thermoplastic norbornene-based resin containing the ethylene-NB copolymer (COC).

Tg of the ethylene-NB copolymer (COC) obtained as described above was 137° C., and the NB unit content was 51 mol %.

[2. Production of Substrates]

In each of Examples 1 to 10 and Comparative Examples 1 and 2, a cycloolefin polymer or cycloolefin copolymer for substrates indicated in Table 1 (pellets of thermoplastic norbornene-based resin: COP-1, COP-5, or COC) was dried at Tg–20° C. for 5 hours. Thereafter, the pellets were injection molded by a standard method using an injection molding machine (FANUC ROBOSHOT® α100B (FANUC ROBOSHOT is a registered trademark in Japan, other countries, or both) produced by FANUC Corporation) with a resin temperature of Tg+150° C., a mold temperature of Tg–10° C., and a holding pressure of 80 MPa to obtain substrates (substrate for channel formation and lid substrate) as molded products having a flat plate shape of 100 mm×100 mm×2 mm.

[3. Formation of Joining Layer on Substrate]

(3-1. Formation of Joining Layer in Examples 1 to 8 and Comparative Examples 1 and 2)

A cyclohexane solution (solution for joining layer) having a solid content concentration of 20 weight % was produced by hermetically sealing 80 parts by weight of cyclohexane (special grade; produced by Wako Pure Chemical Industries, Ltd.) in a glass hermetically sealed vessel (Pyrex® (Pyrex is a registered trademark in Japan, other countries, or both) media bottle produced by Corning Incorporated) with 20 parts by weight of pellets of a thermoplastic norbornene-based resin for a joining layer (COP-2, COP-3, COP-4, or COP-1) indicated in Table 1 and performing shaking thereof at room temperature to cause dissolution.

The obtained solution for a joining layer was cast onto a molded product (substrate for channel formation: COP-1 or COC) having a flat plate shape of 100 mm×100 mm×2 mm that was obtained as described above, and a MINI AUTOMATIC FILM APPLICATOR (produced by Allgood) was used to perform wet coating. The flat plate molded product that had been coated was dried at room temperature for approximately 10 minutes and was then thermally dried in an 80° C. oven for 1 hour to obtain a molded product that was coated with a joining layer (substrate for channel formation on which joining layer had been formed).

(3-2. Formation of Joining Layer in Example 9)

A xylene solution (solution for joining layer) having a solid content concentration of 20 weight % was produced by hermetically sealing 80 parts by weight of xylene (special grade; produced by Wako Pure Chemical Industries, Ltd.) in a glass hermetically sealed vessel (Pyrex® media bottle produced by Corning Incorporated) with 20 parts by weight of pellets of a thermoplastic norbornene-based resin for a joining layer (COP-2) indicated in Table 1 and performing shaking thereof at room temperature to cause dissolution.

The obtained solution for a joining layer was cast onto a molded product (substrate for channel formation: COP-1) having a flat plate shape of 100 mm×100 mm×2 mm that was obtained as described above, and a MINI AUTOMATIC FILM APPLICATOR (produced by Allgood) was used to perform wet coating. The flat plate molded product that had been coated was dried at room temperature for approximately 10 minutes and was then thermally dried in a 120° C. oven for 5 minutes to obtain a molded product that was coated with a joining layer (substrate for channel formation on which joining layer had been formed).

(3-3. Formation of Joining Layer in Example 10)

A cyclohexane solution (solution for joining layer) having a solid content concentration of 20 weight % was produced by hermetically sealing 80 parts by weight of cyclohexane (special grade; produced by Wako Pure Chemical Industries, Ltd.) in a glass hermetically sealed vessel (Pyrex® media bottle produced by Corning Incorporated) with 20 parts by weight of pellets of a thermoplastic norbornene-based resin for a joining layer (COP-3) indicated in Table 1 and performing shaking thereof at room temperature to cause dissolution.

The obtained solution for a joining layer was cast onto a molded product (substrate for channel formation: COP-5) having a flat plate shape of 100 mm×100 mm×2 mm that was obtained as described above, and a MINI AUTOMATIC FILM APPLICATOR (produced by Allgood) was used to perform wet coating. The flat plate molded product that had been coated was dried at room temperature for approximately 10 minutes and was then thermally dried in an 80° C. oven for 5 minutes to obtain a molded product that was coated with a joining layer (substrate for channel formation on which joining layer had been formed).

[4. Channel Cutting of Substrate]

Figure 3A:
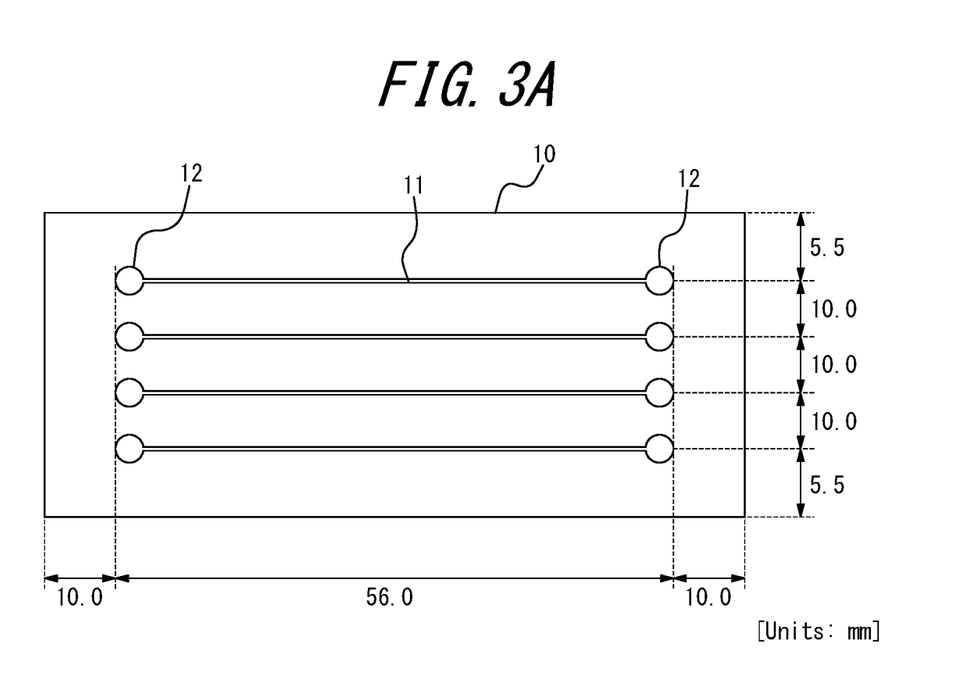
FIG. 3A is a plan view illustrating one example of a channel substrate of a microchannel chip.

The molded product that was coated with a joining layer (substrate for channel formation on which joining layer had been formed) was subjected to channel cutting and external form processing using an ultrahigh precision high-speed microprocessing machine Android II (produced by ROKU—ROKU Sangyo, Ltd.) so as to obtain a channel substrate 10 (thickness: 2.0 mm; external form: 76.0 mm×26.0 mm) on which a joining layer had been formed and that included four channels 11 (width: 100 μm; depth: 100 μm) in a pattern such as illustrated in FIG. 3A on one surface thereof.

Figure 3B:
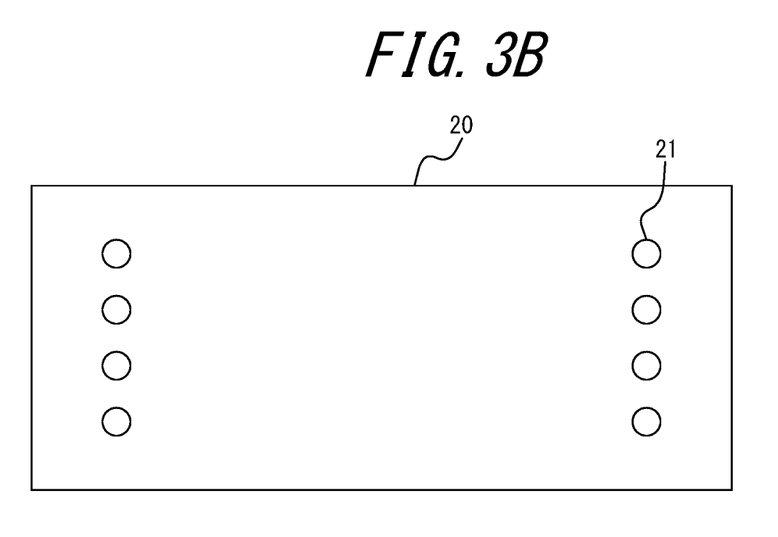
FIG. 3B is a plan view illustrating one example of a lid substrate of a microchannel chip.

Moreover, a lid substrate obtained as described above in "2. Production of substrates" was subjected to formation of 8 through holes 21 (injection ports) of 2.0 mm in diameter as illustrated in FIG. 3B and external form processing so as to obtain a lid substrate 20 (thickness: 2.0 mm; external form: 76.0 mm×26.0 mm). Note that positions of the through holes 21 were set as positions corresponding to ends 12 of the channels 11 on the channel substrate 10.

[5. Mating of Substrates]

The channel substrate on which a joining layer had been formed and the lid substrate were stacked, and then a rubber roll was pressed thereagainst a number of times so as to release trapped air and perform pressure bonding to thereby produce a temporarily fixed assembly A. Note that since a small amount of air bubbles diffuse during autoclave processing, a problem does not arise so long as a large amount of air is not trapped. The temporarily fixed assembly A was loaded into a retort pouch bag (produced by Meiwa Pax Co., Ltd.) and was then subjected to degassed packaging in a vacuum packaging machine (TECNOVAC T1000 produced by Nippon Hoso-Kikai Co., Ltd.). The degassed package was then loaded into an autoclave vessel (DANDELION DL-2010 produced by Hanyuda Co. Jp.) and was subjected to joining and defoaming treatment by autoclaving at a temperature indicated in Table 1 and 0.8 MPa with a heating and pressing time of 90 minutes to obtain a microchannel chip as an assembly.

[6. Evaluation]

<Adhesive Strength>

Adhesive strength was measured in accordance with JIS K 6854-2 (180° peeling). Incisions with a width of 10 mm were made at a sheet (lid substrate) side of an assembly such as to pass through the sheet and an adhesive layer as illustrated in FIG. 3. A section of 10 mm in width where the incisions had been made was peeled from the edge to enable chuck fixing. The molded plate (channel substrate) side was fixed to a lower chuck and the sheet side was fixed to an upper chuck of an oven-equipped universal tester (Autograph AGS-X10 kN produced by Shimadzu Corporation), and the assembly was held therein at room temperature for 5 minutes. After this holding, 180° peeling was performed with a peeling width of 10 mm and a peeling rate of 100 mm/min in order to determine the peel strength, which was taken to be the adhesive strength.

<Liquid Pumping Test>

For each of 5 samples, a pressure control-type pulseless flow pump P-Pump (produced by Takasago Electric, Inc.) was used to inject ink aqueous solution into each channel of a produced microchannel chip via an injection port. The outlet side was sealed with silicone rubber, and the liquid pumping pressure was raised to 650 kPa and held thereat for 3 minutes. Seepage of the ink aqueous solution from the channels into the joint was visually inspected.

<Observation of Joined Cross-Section and Measurement of Joining Layer Thickness>

Cross-sectioning of an obtained assembly (microchannel chip) was performed in cryomilling mode using an Ion Milling System IM4000PLUS (produced by Hitachi High-Tech Corporation). This cross-section was observed using a field emission scanning electron microscope FE-SEM8220 (produced by Hitachi High-Tech Corporation), and the thickness of a joining layer was measured.

<Evaluation of Channel Cross-Section Before and After Steam Sterilization>

(Steam Sterilization)

An obtained assembly (microchannel chip) was subjected to steam sterilization under conditions of 30 minutes at 121° C. and 0.12 MPa using a small high-pressure steam sterilization device.

(Evaluation of Channel Cross-Section)

A field emission scanning electron microscope FE-SEM8220 (produced by Hitachi High-Tech Corporation) was used to measure the cross-sectional area S1 before steam sterilization and the area S2 after steam sterilization. A channel shape retention rate was determined by S2/S1× 100(%).

[7. Evaluation]

The types and glass-transition temperatures Tg of cycloolefin polymers used for substrates (channel substrate and lid substrate) and a joining layer, the thickness of the joining layer, and results of evaluations are shown in Table 1. Symbols for evaluations represent the following meanings.

<Liquid Pumping Test>

O: No seepage x: Seepage

<Evaluation of Channel Cross-Section after Steam Sterilization>

Channel Shape Retention Rate

⊚: 95% or more

O: Not less than 90% and less than 95%

Δ: Not less than 80% and less than 90% x: Less than 80%

TABLE 1

| | | Example 1 | Example 2 | Example 3 | Example 4 | Example 5 | Example 6 | Example 7 | Example 8 | Example 9 | Example 10 | Comparative Example 1 | Comparative Example 2 |
|---|---|---|---|---|---|---|---|---|---|---|---|---|---|
| Cycloolefin polymer for substrates (channel substrate and lid substrate) | Name | COP-1 | COP-1 | COP-1 | COP-1 | COP-1 | COP-1 | COP-1 | COC | COP-1 | COP-5 | COP-1 | COP-1 |
| | Tg [° C.] | 134 | 134 | 134 | 134 | 134 | 134 | 134 | 137 | 134 | 156 | 134 | 134 |
| Cycloolefin polymer for joining layer | Name | COP-2 | COP-2 | COP-2 | COP-2 | COP-2 | COP-3 | COP-4 | COP-2 | COP-2 | COP-3 | COP-2 | COP-1 |
| | Tg [° C.] | 70 | 70 | 70 | 70 | 70 | 104 | 124 | 70 | 70 | 104 | 70 | 134 |
| Tg difference [° C.] | | 64 | 64 | 64 | 64 | 64 | 30 | 10 | 67 | 64 | 52 | 64 | 0 |
| Thickness of joining layer [μm] | | 0.2 | 1 | 5 | 8 | 45 | 1 | 1 | 1 | 1 | 1 | 52 | 0.2 |
| Autoclave joining conditions 90 min, 0.8 MPa | | 110° C. | 110° C. | 110° C. | 110° C. | 110° C. | 120° C. | 130° C. | 110° C. | 110° C. | 120° C. | 110° C. | 135° C. |
| Joint strength | | 24 | 25 | 27 | 27 | 27 | 25 | 25 | 25 | 25 | 25 | 27 | 0.2 |
| Liquid pumping test | | O | O | O | O | O | O | O | O | O | O | O | X |
| Evaluation of channel cross-section after steam sterilization | | ⊚ | ⊚ | ⊚ | O | Δ | O | O | ⊚ | ⊚ | ⊚ | X | — |

INDUSTRIAL APPLICABILITY

According to the present disclosure, it is possible to provide a microchannel chip and method for manufacturing the same with which channel deformation does not occur even when high-temperature and high-pressure sterilization treatment is performed and with which strong joining performance of substrates is maintained.

REFERENCE SIGNS LIST

10 channel substrate
11 channel
12 ends
20 lid substrate
21 through hole

The invention claimed is:

1. A microchannel chip comprising: a channel substrate having a microchannel formed on at least one surface thereof; a lid substrate; and a joining layer joining the channel substrate and the lid substrate, wherein
the channel substrate, the lid substrate, and the joining layer are each formed of a cycloolefin polymer,
a glass-transition temperature $Tg_{s1}$ of a cycloolefin polymer forming the channel substrate, a glass-transition temperature $Tg_{s2}$ of a cycloolefin polymer forming the lid substrate, and a glass-transition temperature $Tg_2$ of a cycloolefin polymer forming the joining layer have relationships:

$Tg_{s1} > Tg_2$; and $Tg_{s2} > Tg_2$, and the joining layer has a thickness of less than 50 μm.

2. The microchannel chip according to claim 1, wherein $Tg_{s1}$ and $Tg_{s2}$ are each 125° C. or higher, $Tg_{s1} \geq Tg_2 + 10°$ C., and $Tg_{s2} \geq Tg_2 + 10°$ C.

3. A method for manufacturing the microchannel chip according to claim 1, comprising joining a channel substrate and a lid substrate via a joining layer by thermal fusion.

4. The method according to claim 3, comprising:
a step of forming a joining layer on at least one of a substrate for channel formation and a lid substrate;
a step of forming a channel on a substrate for channel formation having a joining layer formed thereon or a substrate for channel formation not having a joining layer formed thereon so as to form a channel substrate having a joining layer formed thereon or a channel substrate not having a joining layer formed thereon; and
a step of joining, via a joining layer by thermal fusion, at least one combination among: a combination of a channel substrate having a joining layer formed thereon and a lid substrate not having a joining layer formed thereon; a combination of a channel substrate not having a joining layer formed thereon and a lid substrate having a joining layer formed thereon; and a combination of a channel substrate having a joining layer formed thereon and a lid substrate having a joining layer formed thereon.

5. The method according to claim 3, comprising:
a step of forming a channel substrate having a channel formed on at least one surface thereof;
a step of forming a joining layer on at least one surface of at least one of a channel substrate and a lid substrate at a section of the surface that is not a section corresponding to a channel; and
a step of joining, via a joining layer by thermal fusion, at least one combination among: a combination of a channel substrate having a joining layer formed thereon and a lid substrate not having a joining layer formed thereon; a combination of a channel substrate not having a joining layer formed thereon and a lid substrate having a joining layer formed thereon; and a combination of a channel substrate having a joining layer formed thereon and a lid substrate having a joining layer formed thereon.

* * * * *